United States Patent
Sebillote-Arnaud et al.

[11] Patent Number: 5,891,452
[45] Date of Patent: Apr. 6, 1999

[54] COSMETIC OR DERMATOLOGICAL COMPOSITION CONTAINING AT LEAST ONE ACTIVE PRINCIPLE PRECURSOR AND A CROSSLINKED POLY(2-ACRYLAMIDO-2-METHYLPROPANESULPHONIC ACID) POLYMER NEUTRALIZED TO AT LEAST 90%

[75] Inventors: Laurence Sebillote-Arnaud, L'Hay Les Roses; Raluca Lorant, Thiais, both of France

[73] Assignee: L'Oreal, Paris, France

[21] Appl. No.: 885,596

[22] Filed: Jun. 30, 1997

[30] Foreign Application Priority Data

Jun. 28, 1996 [FR] France .................................. 96 08110

[51] Int. Cl.$^6$ ................................................ A61K 7/48
[52] U.S. Cl. ........................... 424/401; 424/59; 424/62; 424/64; 424/70.1; 424/70.7; 424/70.8; 514/844; 514/845; 514/846; 514/880; 514/881; 514/944
[58] Field of Search ................................. 424/40.1, 70.1, 424/62, 70.7, 70.8, 59, 69; 514/844, 845, 846, 944, 880, 881

[56] References Cited

U.S. PATENT DOCUMENTS

| | | | |
|---|---|---|---|
| 5,114,706 | 5/1992 | Duvel | 424/70 |
| 5,605,694 | 2/1997 | Nadaud | 424/401 |

FOREIGN PATENT DOCUMENTS

A 0 487 404  5/1992  European Pat. Off. .

*Primary Examiner*—Jyothsna Venkat
*Attorney, Agent, or Firm*—Finnegan, Henderson, Farabow & Garrett & Dunner, L.L.P.

[57] ABSTRACT

The invention relates to a cosmetic or dermatological composition containing at least one active principle precursor capable of releasing an active principle by enzymatic reaction on contact with the *Stratum corneum* and at least one crosslinked poly(2-acrylamido-2-methylpropanesulphonic acid) polymer neutralized to at least 90% and to its uses. It generally contains, distributed randomly: (a) from 90 to 99.9% by weight of units of formula (1):

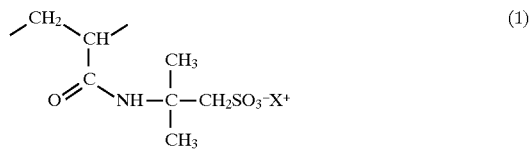

in which $X^+$ denotes a cation or a mixture of cations, it being possible for at most 10 mol % of the cations $X^+$ to be protons $H^+$; and (b) from 0.01 to 10% by weight of crosslinking units resulting from at least one monomer having at least two olefinic double bonds, the proportions by weight being defined with respect to the total weight of the polymer.

27 Claims, No Drawings

COSMETIC OR DERMATOLOGICAL COMPOSITION CONTAINING AT LEAST ONE ACTIVE PRINCIPLE PRECURSOR AND A CROSSLINKED POLY(2-ACRYLAMIDO-2-METHYLPROPANESULPHONIC ACID) POLYMER NEUTRALIZED TO AT LEAST 90%

The invention relates to a cosmetic or dermatological composition containing at least one active principle precursor capable of releasing an active principle by enzymatic reaction on contact with the *Stratum corneum* and at least one crosslinked poly(2-acrylamido-2-methylpropanesulphonic acid) polymer neutralized to at least 90% and to its uses.

There has been an increasing search, for a number of years, to introduce vitamins, such as vitamins A, B, C, D, E and F, and other active principles into cosmetic or dermatological compositions for the purpose of contributing specific treatments against, in particular, excess weight, ageing of the skin, its drying, its pigmentation, acne and some skin diseases such as psoriasis or alternatively for promoting, healing or restructuring of the skin.

In particular, the application of ascorbic acid or vitamin C on the skin, in a sufficient amount, makes it possible to stimulate the growth of connective tissue and in particular that of collagen. Ascorbic acid also makes it possible to reinforce the defences of the cutaneous tissue against external attacks, such as ultraviolet radiation or pollution, and against attacks by medicaments, alcohol or tobacco.

Moreover, tocopherols such as vitamin E are known to possess both antioxidizing properties with respect to phospholipids of the cell membrane and antiradical (AFR) properties (see "Radicaux libres et Vitamine E" [Free radicals and vitamin E] by J. B. Chazan and M. Szulc, Cah. Nutr. Diet., 1987 6 XXII, 1, pages 66–76). In addition, vitamin A or retinol, as well as hydroxy acids, are known for combatting ageing. Moreover, vitamin A is known to provide for healing of the skin.

Unfortunately, the majority of these active principles (vitamins, antioxidants, hydroxy acids and the like) are unstable in solution, sensitive to external factors making these solutions ineffectual and going against the desired effectiveness. In particular, the article "Stability of ascorbic acid" by Br. Hajratwala, which appeared in "Sciences Pharmaceutiques Revue", pages 281–286, teaches that ascorbic acid has properties of instability in aqueous medium, in aerobic and anaerobic medium, with a more pronounced instability in aerobic medium. This article illustrates in particular the behaviour of ascorbic acid in the face of variations in the pH of the solution containing it, variations in light and variations in temperature, and in the face of compounds such as surfactants, solvents or catalysts, in particular metal catalysts.

Various means have consequently been envisaged for stabilizing ascorbic acid. Among these means, Japanese Patents JP 89/115,558 and JP 83/129,892 teach the blocking of the reactive site of ascorbic acid, namely the hydroxyl site, by esterification or etherification with in particular phosphate, sulphate or alkyl derivatives and the use of the derivatives in cosmetic compositions to act as vitamin C.

Unfortunately, the latter are much less effective than free vitamin C, that is to say, without additional groups. To this end, the use of a precursor of vitamin C has been envisaged. Thus, European Patent EP 487,404 discloses the use of a glucosyl derivative in dermatological compositions which is capable of releasing ascorbic acid when these compositions are brought into contact with the skin.

Moreover, the esterification of an ascorbic acid derivative and of a tocopherol derivative with phosphoric acid (see the document "Bioconversion of a vitamin to vitamins C and E in skin" by Kakuji Tojo and Ae-Ric. Lee, published in J. Cosmet. Chem., 38, pages 333–339) and its use in a composition have been envisaged.

However, this diester, with respect to ascorbic acid, is less effective than free ascorbic acid and, with respect to vitamin E, has a poorer antioxidizing activity than free vitamin E. This same problem is also encountered for any type of active principle.

The need consequently remains for a stable cosmetic or dermatological composition which makes possible the release, with a good yield, from a precursor, of a significant amount of active principle by enzymatic hydrolysis on contact with the *stratum corneum*.

Moreover, cosmetic or dermatological compositions generally exhibit a high viscosity and are mostly formulated in a thickened liquid form, such as a milk, a cream, a gel or a paste. This type of presentation is much appreciated by the consumer; it is more often than not a practical worry for the formulator: to facilitate uptake of the product outside its packaging without significant loss, to restrict the spreading of the product to the local treatment region and to be able to use it in amounts which are sufficient to produce the desired cosmetic or dermatological effect.

This objective is important for formulations such as those of care, hygiene or make-up products which must spread well and homogeneously over the local area to be treated. To satisfy these conditions, the viscosity of the compositions is increased by the addition of thickening or gelling polymers.

The active principle precursors as described above can be incorporated with difficulty in cosmetic or dermatological formulations in the presence of the thickening or gelling polymers currently used. These polymers, on contact with the said active principle precursors, generally lose their thickening or gelling power and do not make it possible to obtain formulations of high and stable viscosity. Moreover, the increase in the concentration of thickening polymer, for the purpose of stabilizing the formulation based on active principle precursors, usually results in undesirable effects at the cosmetic level, such as a runny effect or a not very attractive appearance.

Poly(2-acrylamido-2-methylpropanesulphonic acid) homopolymers, such as the commercial products COSMEDIA HSP1 160 and RHEOTIK 8011 from the company Henkel, are known in the state of the art. They are used as thickening or gelling agents in numerous cosmetic formulations. These polymers do not make it possible to obtain, in the presence of active principle precursors, stable and homogeneous compositions which can reach high viscosities in a wide pH range. They result, more often than not, in fluid, heterogeneous, stringy and runny gels.

The inventors have surprisingly discovered a new family of thickening or gelling polymers making it possible to obtain stable thickened cosmetic and dermatological formulations, based on active principle precursors, making it possible to treat keratinous substances effectively while also providing for a good yield in the enzymatic hydrolysis of the precursor of the active principle.

Moreover, these specific polymers make it possible to produce homogeneous cosmetic or dermatological products which can reach high viscosities which are stable over time at room temperature or at higher temperatures. Finally, they make it possible to produce gels which are transparent, non-runny, non-stringy, soft and smooth on application.

The subject of the invention is consequently a cosmetic or dermatological composition containing, in a cosmetically acceptable medium, at least one active principle precursor capable of releasing an active principle by enzymatic reaction on contact with the *stratum corneum* and at least one crosslinked poly(2-acrylamido-2-methylpropanesulphonic acid) neutralized to at least 90%.

The composition of the invention has a certain consistency or behavior; it is not stringy, that is to say that it does not form strings when taken up with the finger. It is more especially provided in the form of a gel.

The crosslinked and virtually or completely neutralized poly(2-acrylamido-2-methylpropanesulphonic acid) polymers in accordance with the invention are water-soluble or swellable in water. They are in general characterized in that they comprise, distributed randomly:

(a) from 90 to 99.9% by weight, relative to the weight of said at least one crosslinked polymer, of units of following formula (1):

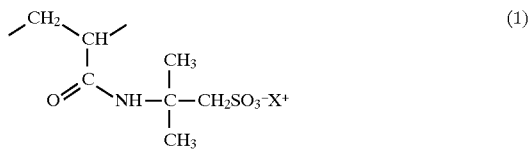

in which $X^+$ denotes a cation or a mixture of cations, it being possible for at most 10 mol % of the cations $X^+$ to be protons $H^+$; and (b) from 0.01 to 10% by weight, relative to the weight of said at least one crosslinked polymer, of crosslinking units resulting from at least one monomer having at least two olefinic double bonds.

The more particularly preferred polymers according to the invention comprise from 98 to 99.5% by weight of units of formula (1) and from 0.2 to 2% by weight of crosslinking units.

The polymers of the invention preferably contain a number of units of formula (1) in an amount which is sufficiently high to produce a hydrodynamic volume of the polymer in solution in water having a radius ranging from 10 to 500 nm, with a homogeneous and unimodal distribution.

$X^+$ represents a cation or a mixture of cations selected in particular from a proton, an alkali metal cation, a cation equivalent to that of an alkaline-earth metal or the ammonium ion.

More particularly, 90 to 100 mol % of the cations are $NH_4^+$ cations and 0 to 10 mol % are protons ($H^+$).

The crosslinking monomers having at least two olefinic double bonds are selected, for example, from dipropylene glycol diallyl ether, polyglycol diallyl ether, triethylene glycol divinyl ether, hydroquinone diallyl ether, tetraallyloxethanoyl or other allyl or vinyl ethers, polyfunctional alcohols, tetraethylene glycol diacrylate, triallylamine, trimethylolpropane diallyl ether, methylenebisacrylamide or divinylbenzene.

The crosslinking monomers having at least two olefinic double bonds are more particularly selected from those corresponding to the following formula (2):

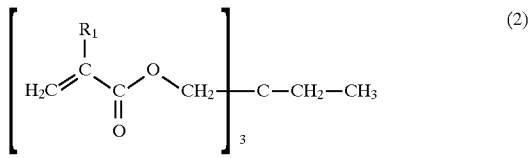

in which $R_1$ denotes a hydrogen atom or a $C_1$–$C_4$ alkyl. The crosslinking monomer is more particularly methyl (trimethylolpropane triacrylate).

The polymerization reaction of the polymers of the invention produces not only linear chains but also branched or crosslinked molecules of polymer. These molecules can be characterized in particular by their rheological behaviour in water but more particularly by dynamic light scattering.

In the case of the characterization of the molecules by dynamic light scattering, the distribution of the hydrodynamic volume of the structures of the polymer is measured. Macromolecules dissolved in water are flexible and surrounded by a salvation envelope formed from water molecules. With charged polymers, such as those of the invention, the size of the molecules depends on the amount of salt in the water. In polar solvents, the uniform charge along the main chain of the polymer results in a significant expansion of the polymeric chain. The fact of increasing the amount of salt increases the amount of electrolyte in the solvent and screens the uniform charges of the polymer. In addition to the molecules transported in the solvation envelope, solvent molecules are fixed in the cavities of the polymer. In this case, the solvent molecules form part of the dissolved macromolecules and move at the same average speed. Thus, the hydrodynamic volume describes the linear dimension of the macromolecule and of these salvation molecules.

The hydrodynamic volume $v_h$ is determined by the following formula:

$$V_h = M/N_A \times (V_2 + dV_1)$$

with:

M denoting the mass in grams of the undissolved macromolecule;

$N_A$ denoting Avogadro's number;

$V_1$ denoting the specific volume of the solvent;

$V_2$ denoting the specific volume of the macromolecule;

d denoting the mass in grams of the solvent which is associated with 1 gram of undissolved macromolecule.

If the hydrodynamic particle is spherical, it is then easy to calculate the hydrodynamic radius from the hydrodynamic volume by the formula:

$$V_h = 4\pi R^3/3$$

with R denoting the hydrodynamic radius.

Cases where hydrodynamic particles are perfect spheres are extremely rare. The majority of synthetic polymers involve compacted structures or ellipsoids of high eccentricity. In this case, the radius is determined with respect to a sphere which is equivalent from a frictional viewpoint to the shape of the particle under consideration.

As a general rule, the determination is carried out with respect to distributions of molecular weight and thus with respect to distributions of hydrodynamic radius and volume. For polydispersed systems, it is necessary to calculate the distribution of the diffusion coefficients. From this distribution, the results relating to the radial distribution and to the distribution of the hydrodynamic volumes are deduced therefrom.

The hydrodynamic volumes of the polymers of the invention are in particular determined by dynamic light scattering from the Stokes-Einstein diffusion coefficients D of formula: $D = kT/6\pi\eta R$ where k is Boltzmann's constant, T is the absolute temperature in degrees Kelvin, $\eta$ is the viscosity of the solvent (water) and R is the hydrodynamic radius.

These diffusion coefficients D are measured according to the method of characterization of a mixture of polymers by laser scattering described in the following references:

(1) Pecora, R; Dynamic Light Scattering; Plenium Press, New York, 1976;

(2) Chu, B; Dynamic Light Scattering; Academic Press, New York, 1994;

(3) Schmitz, KS; Introduction to Dynamic Light Scattering; Academic Press, New York, 1990;

(4) Provincher S. W.; Comp. Phys., 27, 213, 1982;

(5) Provincher S. W.; Comp. Phys., 27, 229, 1982;

(6) ALV Laservertriebgesellschaft mhH, Robert Bosch Str. 47, D-63225 Langen, Germany;

(7) ELS-Reinheimer Strasse 11, D-64846 Gross-Zimmern, Germany; and (8) Chi Wu et al., Macromolecules, 1995, 28, 4914–4919.

The particularly preferred polymers are those exhibiting a viscosity, measured with a Brookfield viscometer in a 2% solution in water at 25° C., of greater than or equal to 1000 cPs and more preferably ranging from 5000 to 40,000 cPs and still more preferably from 6500 to 35,000 cPs.

The crosslinked poly(2-acrylamido-2-methylpropanesulphonic acid) of the invention can be obtained according to the preparation process comprising the following stages:

(a) the 2-acrylamido-2-methylpropanesulphonic acid monomer is dispersed or dissolved in the free form in a tert-butanol or water and tert-butanol solution;

(b) the solution or the dispersion of AMPS monomer obtained in (a) is neutralized with one or a number of inorganic or organic bases, preferably ammonia $NH_3$, in an amount which makes it possible to obtain a degree of neutralization of the sulphonic acid functional groups of the polymer ranging from 90 to 100%;

(c) the crosslinking monomer or monomers is/are added to the solution or dispersion obtained in (b); and (d) a conventional radical polymerization is carried out in the presence of free radical initiators at a temperature ranging from 10° to 150° C., the polymer precipitating in the solution or dispersion based on tert-butanol.

The at least one crosslinked, virtually or totally neutralized poly(2-acrylamido-2-methylpropanesulphonic acid) polymer is present in the cosmetic or dermatological compositions of the invention in concentrations preferably ranging from 0.01 to 20% by weight with respect to the total weight of the composition and more preferably from 0.1 to 10% by weight.

According to the invention, the active principle precursors can be selected from phosphates; sulphates; active principle alkyl or acyl esters; acyl or alkyl ethers; active principle amides and active principle monosaccharide derivatives. They can be used alone or as mixtures.

The acyl and alkyl radicals have in particular from 1 to 30 carbon atoms. In particular, the alkyl or acyl esters and ethers can result from the reaction with an inorganic acid, such as a sulphate or a phosphate, in order to react with a sulfatase or phosphatase on contact with the skin, or else result from the reaction with an organic acid, such as palmitic, acetic, propionic, nicotinic, 1,2,3-propanetricarboxylic or ferulic acid, in order to react with a specific esterase of the skin.

According to the invention, the precursors capable of releasing an active principle by enzymatic hydrolysis on contact with the skin are preferably selected from vitamin precursors, such as those of vitamin A (retinol), of vitamin B, of vitamin C (ascorbic acid), of vitamin D, of vitamin E (tocopherol) or of vitamin F; hydroxy acid precursors such as those of lactic acid or of glycolic acid; quercetin precursors; nucleotide precursors; phosphated hydroxyacetones; glycerol precursors and their mixtures.

By way of example for vitamins, mention may be made, as precursors, of the phosphates, the sulphates, a palmitate, an acetate, a nicotinate or a propionate and the monosaccharide derivatives of vitamin A (retinol), C (ascorbic acid) or E (tocopherol).

Use may be made, as ascorbic acid phosphate, of the ascorbylphosphate of an alkali, alkaline-earth or transition metal, such as magnesium, sodium, potasssium, calcium or zinc. Use may be made, as retinol phosphate, of the retinylphosphate of an alkali or alkaline-earth metal, such as magnesium or potassium.

Use may be made, as organic acid ester of vitamin C, of a palmitic, acetic or propionic ester grafted in the 2 or 3 position of vitamin C. Use may be made, as tocopherol ester, of tocopherol nicotinates or acetates. Use may be made, among retinol esters, of an ester of palmitic, propionic or acetic acid.

Mention may be made, by way of example among the monosaccharide derivatives of vitamin C which can be used in the invention, of glucosylated, mannosylated, fructosylated or N-acetylglucosaminated vitamin C, the N-acetylmuramic derivative of vitamin C, the fucosylated or galactosylated derivative or their mixtures.

Moreover, by way of example for lactic acid (α-hydroxy acid), mention may be made of glycerol trilactate, ethyl lactate and sulphated derivatives of lactic acid. Moreover, by way of example for glycerol, mention may be made of glycerol trilactate and β-glycerophosphates in order to release glycerol on contact with the skin.

Still by way of example, mention may be made, as quercetin precursors, of glucosylquercetin and of a quercetin ester, such as quercetin ferulate, in order to release quercetin synergistically. Mention may be made, among nucleotide precursors, of adenosine phosphate, guanosine phosphate, cytosine phosphate, uridine phosphate, thymidine phosphate, inosine phosphate or xanthosine phosphate.

The particularly preferred active principle precursors of the invention are phosphate derivatives of vitamin C and more preferentially the transition metal salts of ascorbylphosphate, where the transition metal is, for example, magnesium, sodium, potassium, calcium or zinc.

The active principle precursor or precursors are present in concentrations preferably ranging from 0.01% to 10% by weight and more preferably from 0.01% to 1% by weight with respect to the total weight of the composition.

The compositions of the invention contain a cosmetically acceptable aqueous medium, that is to say a medium compatible with all keratinous substances, such as the skin, nails, mucous membranes and hair, or any other cutaneous region of the body.

The compositions preferably contain a cosmetically or dermatologically acceptable aqueous medium. They exhibit a pH which can preferably range from 1 to 13 and more preferentially from 2 to 12.

The cosmetically or dermatologically acceptable medium of the compositions according to the invention is preferably composed of water and optionally of cosmetically or dermatologically acceptable organic solvents which exhibit acceptable tolerance, acceptable toxicology and acceptable feel.

The organic solvents can represent from 5% to 98% of the total weight of the composition. They can be selected from hydrophilic organic solvents, lipophilic organic solvents, amphiphilic solvents and mixtures thereof.

Among the hydrophilic organic solvents, mention may be made, for example, of linear or branched lower monoalcohols having from 1 to 8 carbon atoms, such as ethanol, propanol, butanol, isopropanol and isobutanol; polyethylene glycols having from 6 to 80 ethylene oxides; polyols such as propylene glycol, isoprene glycol, butylene glycol, glycerol and sorbitol; mono- or dialkyl isosorbides in which the alkyl groups have from 1 to 5 carbon atoms, such as dimethyl isosorbide; glycol ethers such as diethylene glycol monomethyl or monoethyl ether and propylene glycol ethers such as dipropylene glycol methyl ether.

Among the amphiphilic organic solvents, mention may be made, for example, of polyols such as polypropylene glycol (PPG) derivatives, for instance polypropylene glycol esters of fatty acid and PPG ethers of fatty alcohol, for instance PPG-36 oleate, PPG-23 oleyl ether. Lipophilic organic solvents which may be mentioned, for example, are fatty esters such as diisopropyl adipate, dioctyl adipate and alkyl benzoates.

In order for the cosmetic or dermatological compositions of the invention to be more pleasant to use, i.e., softer on application, more nourishing, more emollient, it is possible to add a fatty phase to the medium of these compositions. The fatty phase preferably represents from 0% to 50% of the total weight of the composition.

This fatty phase can contain one or a number of oils preferably selected from:

- water-soluble or water-insoluble, organomodified or non-organomodified, linear, branched or cyclic, volatile or non-volatile silicones;
- mineral oils, such as liquid paraffin and liquid petrolatum;
- oils of animal origin, such as perhydrosqualene;
- oils of plant origin, such as sweet almond oil, avocado oil, castor oil, olive oil, jojoba oil, sesame oil, groundnut oil, macadamia oil, grape seed oil, rapeseed oil or coconut oil;
- synthetic oils, such as purcellin oil or isoparaffins;
- fluorinated and perfluorinated oils; and
- esters of fatty acids, such as purcellin oil.

It can also contain, as fatty substance, one or a number of fatty alcohols, fatty acids such as stearic acid or waxes such as paraffin wax, polyethylene waxes, carnauba wax and beeswax.

All the compositions of the invention may contain adjuvants that are common in the cosmetic and dermatological fields: other conventional hydrophilic or lipophilic gelling agents or thickeners; hydrophilic or lipophilic active principles; preservatives; antioxidants; fragrances; emulsifiers; moisturizing agents; emollients; sequestering agents; surfactants; polymers; basifying or acidifying agents; fillers; agents for combatting free radicals; ceramides; sunscreen agents, in particular ultraviolet screening agents; insect repellents; slimming agents; colouring materials; bactericides; and antidandruff agents. The amounts of these various adjuvants are those conventionally used in the fields under consideration.

Obviously, a person skilled in the art will take care to choose the possible compound or compounds to be added to the composition according to the invention so that the advantageous properties intrinsically attached to the composition in accordance with the invention are not, or not substantially, detrimentally affected by the envisaged addition.

The compositions according to the invention can be provided in all the forms appropriate for a topical application, in particular in the form of solutions of the lotion or serum type, in the form of aqueous gels or in the form of emulsions obtained by dispersion of a fatty phase in an oil-in-water phase (O/W) or a water in oil phase (W/O), with a liquid, semi-liquid or solid consistency, such as milks, more or less smooth creams, or pastes. These compositions are prepared according to the usual methods.

The compositions according to the invention can be used as rinse-out hair products or as leave-in hair products, in particular for washing, caring for, conditioning or form retention of the hairstyle or shaping keratinous fibres, such as the hair.

They can be styling products, such as hair-setting lotions, blow-drying lotions or fixing and styling compositions. The lotions can be packaged in various forms, in particular in vaporizers or pump-action sprays or in aerosol containers, in order to provide for application of the composition in the vaporized form or in the foam form. Such packaging forms are indicated, for example, when it is desired to obtain a spray or a foam for fixing or treating the hair.

The compositions of the invention can also be shampoos or compositions of a rinse-out or leave-in nature to be applied before or after shampooing, dyeing, bleaching, perming or hair straightening.

The compositions of the invention can also be used as care or hygiene product, such as protection, treatment or care creams for the face, for the hands or for the body, protection or care body milks or lotions, gels or foams for caring for the skin and mucous membranes or for cleansing the skin.

The compositions of the invention can also be used as anti-sun product.

The compositions can also comprise solid preparations constituting cleansing bars or soaps.

The compositions of the invention can also be used as oral care product, such as toothpastes.

The compositions can be make-up products.

Another subject of the invention is a process for the non-therapeutic cosmetic treatment of the skin, scalp, hair, eyelashes, eyebrows, nails or mucous membranes, in particular for combatting blackheads in greasy skins, for promoting hair growth, for preventing ageing of the skin, its drying or its pigmentation, for promoting healing or restructuring of the skin or for stimulating the growth of the connective tissues of the epidermis. It is characterized in that a composition as defined above is applied on the keratinous substrate according to the usual technique for the use of this composition. For example: application of creams, gels, serums, lotions or milks on the skin, the scalp or the mucous membranes. The type of treatment depends on the active principle precursor or precursors present in the composition.

A further subject of the invention is the use of the above composition for preparing a lotion, a serum, a milk, a pomade or an ointment intended for the therapeutic treatment of keratinous substances, such as the skin, scalp, hair, eyelashes, eyebrows, nails or mucous membranes, in particular for combatting acne and blackheads in greasy skins, for combatting hair loss, for combatting certain diseases of the skin such as psoriasis, for combatting ageing of the skin, its drying or its pigmentation, for promoting healing or restructuring of the skin or for stimulating the growth of the connective tissues of the epidermis.

The following examples illustrate the invention without having a limiting nature.

PREPARATION EXAMPLE A 2006.2 g of tert-butanol were introduced into a 5-liter round-bottomed flask equipped with a stirrer, a reflux condenser, a thermometer and a device for introducing nitrogen and ammonia, followed by 340.0 g of 2-acrylamido-2-methylpropanesulphonic acid, which was dispersed in the solution with vigorous stirring. After 30 minutes, ammonia was added via the upper pipe of the round-bottomed flask and the reaction mixture was maintained for 30 minutes at room temperature until a pH of the order of 6–6.5 is obtained. 32.0 g of a 25% solution of trimethylolpropane triacrylate in tert-butanol were then introduced and the reaction mixture was heated to 60° C. while simultaneously being made inert by introduction of nitrogen into the round-bottomed flask. Once this temperature was reached, dilauroyl peroxide was added. The reaction began immediately, which was reflected by a rise in temperature and by precipitation of the polymerisate. Fifteen minutes after the polymerization began, a stream of nitrogen was introduced. Thirty minutes after the addition of the initiator, the temperature of the reaction mixture reached a maximum of 65°–70° C. 30 minutes after having reached this temperature, the reaction mixture was heated to reflux and was maintained under these conditions for 2 hours. During the reaction, the formation of a thick paste was observed.

The reaction mixture was cooled to room temperature and the product obtained was filtered off. The recovered paste was then dried under vacuum at 60°–70° C. for 24 hours. 391 g of crosslinked and neutralized poly(2-acrylamido-2-methylpropanesulphonic acid) polymer were obtained with a viscosity, measured with a Brookfield viscometer, rotor 4, at a rotational speed of 100 revolutions/minute in a 2% solution in water at 25° C., ranging from 15,000 cPs to 35,000 cPs. The viscosity of the polymer may chosen and controlled according to conventional means, depending on the cosmetic application envisaged.

The hydrodynamic radius of the polymer obtained in an aqueous solution, determined by dynamic light scattering, was 440 nm.

PREPARATION EXAMPLE B 2006.2 g of tert-butanol were introduced into a 5-liter round-bottomed flask equipped with a stirrer, a reflux condenser, a thermometer and a device for introduction of nitrogen and ammonia, followed by 340.0 g of 2-acrylamido-2-methylpropanesulphonic acid, which was dispersed in the solution with vigorous stirring. After 30 minutes, ammonia was added via the upper pipe of the round-bottomed flask and the reaction mixture was maintained for 30 minutes at room temperature until a pH of the order of 6–6.5 was obtained. 19.2 g of a 25% solution of trimethylolpropane triacrylate in tert-butanol were then introduced and the reaction mixture was heated to 60° C. while simultaneously being made inert by introduction of nitrogen into the round-bottomed flask. Once this temperature was reached, dilauroyl peroxide was added. The reaction began immediately, which was reflected by a rise in temperature and by precipitation of the polymerizate. Fifteen minutes after the polymerization began, a stream of nitrogen was introduced. Thirty minutes after the addition of the initiator, the temperature of the reaction mixture reached a maximum of 65°–70° C. Thirty minutes after having reached this temperature, the reaction mixture was heated to reflux and was maintained under these conditions for 2 hours. During the reaction, the formation of a thick paste was observed.

The reaction mixture was cooled to room temperature and the product obtained was filtered off. The recovered paste was then dried under vacuum at 60°–70° C. for 24 hours. 391 g of crosslinked and neutralized poly(2-acrylamido-2-methylpropanesulphonic acid) were obtained with a viscosity, measured with a Brookfield viscometer, rotor 4, at a rotational speed of 100 revolutions/minute in a 2% solution in water at 25° C., of the order of 7000 cPs.

The hydrodynamic radius of the polymer obtained in an aqueous solution, determined by dynamic light scattering, was 160 nm.

EXAMPLE 1

Lightening gel

Crosslinked poly(2-acrylamido-2-methylpropanesulphonic acid) neutralized with ammonia, prepared according to the process of Preparation Example B, with a viscosity of the order of 7000 cPs in a 2% solution in water at 25° C. 1.5% AM Magnesium ascorbylphosphate 0.3%

Preservative q.s.

Distilled water q.s. for 100%

A stable, thick, smooth and homogeneous gel was obtained.

EXAMPLE 2

Refreshing gel for greasy skins

Crosslinked poly(2-acrylamido-2-methylpropanesulphonic acid) neutralized with ammonia, prepared according to the process of Preparation Example A with a viscosity of the order of 16,000 cPs in a 2% solution in water at 25° C. 2 g AM Magnesium ascorbylphosphate 1 g Glycerol 3 g Preservative q.s.

Distilled water q.s. for 100 g

A gel was obtained which is thick, completely transparent, soft and fresh on the skin, non-runny and non-stringy on being taken up.

Comparison With A Composition Of The Prior Art

Upon replacement of the crosslinked poly(2-acrylamido-2-methylpropanesulphonic acid) polymer with a non-crosslinked homopolymer of 2-acrylamido-2-methylpropanesulphonic acid, such as the commercial product COSMEDIA HSP1 160 sold by Henkel, a product was obtained which has unacceptable cosmetic properties: fluid appearance, runny, stringy on being taken up and sticky to the touch.

EXAMPLE 3

Vitamin care cream-gel

Fatty phase

Sweet almond oil 4.0 g

Cyclomethicone 2.0 g

Tocopherol acetate 1.0 g

Aqueous phase

Crosslinked poly(2-acrylamido-2-methylpropanesulphonic acid) neutralized with ammonia, prepared according to the process of Preparation Example A with a viscosity of the order of 16,000 cPs in a 2% solution in water at 25° C. 1.5 g AM Magnesium ascorbylphosphate 1.0 g Glycerol 3.0 g Preservative q.s.

Distilled water q.s. for 100 g

A fairly thick, non-runny, smooth and glossy cream with a pH of 7 was obtained.

Comparison With A Composition Of The Prior Art

Upon replacement of the crosslinked poly(2-acrylamido-2-methylpropanesulphonic acid) polymer with a non-crosslinked homopolymer of 2-acrylamido-2-methylpropanesulphonic acid, such as the commercial product Cosmedia HSP1160 sold by Henkel, a coarse and unstable dispersion with a heterogeneous appearance was obtained. It was not possible to prepare thick and non-runny products, whatever the homopolymer concentration.

EXAMPLE 4

Smoothing cream for the face

Fatty phase

Soybean oil 7.0 g

Hydrogenated polyisobutene 5.0 g

Tocopherol acetate 0.5 g

Aqueous phase

Crosslinked poly(2-acrylamido-2-methylpropanesulphonic acid) neutralized with ammonia, prepared according to the process of Preparation Example A with a viscosity of the order of 16,000 cPs in a 2% solution in water at 25° C. 1.5 g AM Glucopyranosyl-L-ascorbic acid 1.0 g Glycerol 3.0 g Preservative q.s.

Distilled water q.s. for 100 g

A white, smooth and glossy cream with a pH of 2.7 was obtained.

What is claimed is:

1. A cosmetic or dermatological composition, said composition comprising, in a cosmetically and dermatologically acceptable medium, at least one active principle precursor which releases an active principle by enzymatic reaction on contact with the *Stratum corneum* and at least one crosslinked poly(2-acrylamido-2-methylpropanesulphonic acid) polymer neutralized to at least 90%, wherein said active principle precursor is selected from the group consisting of:

phosphates, sulphates, palmitates, acetates, nicotinates, propionates and monosaccharide derivatives of vitamin A, vitamin C and vitamin E, wherein when said monosaccharide derivatives are derivatives of vitamin C, said monosaccharide derivatives of vitamin C are selected from the group consisting of glucosylated, mannosylated, fructosylated or N-acetylglucosaminated vitamin C, N-acetylmuramic derivatives of vitamin C, fucosylated or galactosylated derivatives of vitamin C and mixtures thereof:

hydroxy acid precursors selected from the group consisting of glycerol trilactate, ethyl lactate and sulphated derivatives of lactic acid;

glycerol precursors selected from the group consisting of β-glycerophosphates;

quercetin precursors selected from the group consisting of glucosylquercetin and quercetin ferulate; and nucleotide precursors selected from the group consisting of adenosine phosphate, guanosine phosphate, cytosine phosphate, uridine phosphate, thymidine phosphate, inosine phosphate and xanthosine phosphate, and further wherein said at least one crosslinked poly(2-acrylamido-2-methylpropanesulphonic acid) polymer comprises, randomly distributed:

(a) from 90 to 99.9% by weight, relative to the weight of said at least one crosslinked polymer, of units of formula (1) below:

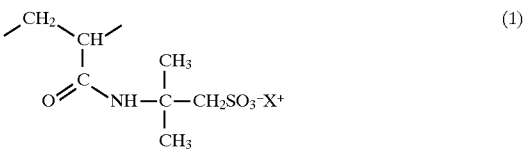

in which $X^+$ denotes a cation or a mixture of cations, it being possible for not more than 10 mol % of the cations $X^+$ to be protons $H^+$; and (b) from 0.01 to 10% by weight, relative to the weight of said at least one crosslinked polymer, of crosslinking units originating from at least one monomer having at least two olefinic double bonds, wherein said at least one monomer is dipropylene glycol diallyl ether, polyglycol diallyl ether, triethylene glycol divinyl ether, hydroquinone diallyl ether; tetraethylene glycol diacrylate, triallylamine, trimethylolpropane diallyl ether, or a compound corresponding to formula (2) below:

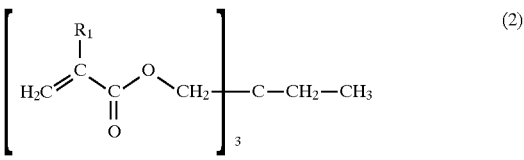

in which $R_1$ denotes a hydrogen atom or a $C_1$–$C_4$ alkyl.

2. A composition according to claim 1, wherein said at least one crosslinked poly(2-acrylamido-2-methylpropanesulphonic acid) polymer contains a number of units of formula (1) in an amount which is sufficiently high to produce a hydrodynamic volume of the polymer in solution in water having a radius ranging from 10 to 500 nm, with a homogeneous and unimodal distribution.

3. A composition according to claim 1, wherein said at least one crosslinked poly(2-acrylamido-2-methylpropanesulphonic acid) polymer contains from 98 to 99.5% by weight of units of formula (1) and from 0.2 to 2% by weight of crosslinking units.

4. A composition according to claim 1, wherein, in the formula (1), the cation $X^+$ is $NH_4^+$.

5. A composition according to claim 1, wherein said at least one crosslinked poly(2-acrylamido-2-methylpropanesulphonic acid) polymer is crosslinked with trimethylolpropane triacrylate.

6. A composition according to claim 1, wherein the polymers of formula (1), when present in an aqueous solution at a concentration of 2%, have a viscosity, measured with a Brookfield viscometer, rotor 4, speed 100 revolutions/minute at 25° C., of greater than or equal to 1000 cps.

7. A composition according to claim 6, wherein said at least one crosslinked poly(2-acrylamido-2-methylpropanesulphonic acid) polymer exhibits a viscosity ranging from 5000 to 40,000 cPs.

8. A composition according to claim 7, wherein said at least one crosslinked poly(2-acrylamido-2-methylpropanesulphonic acid) polymer exhibits a viscosity ranging from 6500 to 35,000 cPs.

9. A composition according to claim 1, wherein said at least one crosslinked poly(2-acrylamido-2-methylpropanesulphonic acid) polymer is present in a concentration ranging from 0.01 to 20% by weight with respect to the total weight of the composition.

10. A composition according to claim 9, wherein said at least one crosslinked poly(2-acrylamido-2-methylpropanesulphonic acid) polymer is present in a concentration ranging from 0.1 to 10% by weight with respect to the total weight of the composition.

11. A composition according to claim 1, wherein said at least one active principle precursor is a phosphate derivative of vitamin C.

12. A composition according to claim 1, wherein said at least one active principle precursor is a transition metal salt of ascorbylphosphate.

13. A composition according to claim 1, wherein said at least one active principle precursor is present in a concentration ranging from 0.01% to 10% by weight with respect to the total weight of the composition.

14. A composition according to claim 13, wherein said at least one active principle precursor is present in a concentration ranging from 0.01% to 1% by weight with respect to the total weight of the composition.

15. A composition according to claim 1, wherein said cosmetically or dermatologically acceptable medium is composed of water or of water and of at least one organic solvent selected from the group consisting of hydrophilic organic solvents, lipophilic organic solvents, amphiphilic solvents and mixtures thereof.

16. A composition according to claim 15, wherein said at least one organic solvent is a mono- or polyfunctional alcohol, an oxyethylenated polyethylene glycol, a propylene glycol ester, sorbitol or a derivative thereof, a dialkyl isosorbide, a glycol ether, a propylene glycol ether, or a fatty ester.

17. A composition according to claim 15, wherein said at least one organic solvent represents from 5% to 98% of the total weight of the composition.

18. A composition according to claim 1, wherein said composition additionally comprises at least one fatty phase.

19. A composition according to claim 18, wherein said at least one fatty phase represents up to 50% of the total weight of the composition.

20. A composition according to claim 1, wherein said composition additionally contains at least one additive selected from the group consisting of conventional hydrophilic or lipophilic gelling or thickening agents hydrophilic or lipophilic active principles, preservatives, antioxidants, fragrances, emulsifiers, moisturizing agents, pigmenting agents, depigmenting agents, keratolytic agents, vitamins, emollients, sequestering agents, surfactants, polymers, basifying or acidifying agents, fillers, agents for combating free radicals, ceramides, sunscreen agents, insect repellents, slimming agents, coloring materials, bactericides, and anti-dandruff agents.

21. A composition according to claim 20, wherein said sunscreen agents are ultraviolet screening agents.

22. A method for washing, caring for, conditioning or promoting form retention of the hairstyle or shaping the hair, said method comprising applying an effective amount of a composition according to claim 1 to the hair as a rinse-out or leave-in hair product.

23. A process for the non-therapeutic cosmetic treatment of the skin, scalp, hair, eyelashes, eyebrows, nails or mucous membranes, wherein an effective amount of a composition as defined according to claim 1 is applied onto said skin, scalp, hair, eyelashes, eyebrows, nails or mucous membranes.

24. A process according to claim 23, wherein said composition is a care product, a hygiene product, a make-up product, or an anti-sun product.

25. A process for the care and hygiene of the mouth, said process comprising placing an effective amount of a composition according to claim 1 in the mouth as an oral care product.

26. A process for the therapeutic treatment of the skin, scalp, hair, eyelashes, eyebrows, nails or mucous membranes, wherein an effective amount of a composition as defined according to claim 1 is applied onto said skin, scalp, hair, eyelashes, eyebrows, nails or mucous membranes.

27. A process according to claim 26, wherein said composition is a care product, a hygiene product, a make-up product, or an anti-sun product.

* * * * *

UNITED STATES PATENT AND TRADEMARK OFFICE
CERTIFICATE OF CORRECTION

PATENT NO.: 5,891,452
DATED: April 6, 1999
INVENTOR(S): Sebillote-Arnaud et al.

It is certified that an error appears in the above-identified patent and that said Letters Patent is hereby corrected as shown below:

IN THE CLAIMS:

Claim 1, col. 11, line 33, "*comeum*" should read --*corneum*--.

Signed and Sealed this

Thirty-first Day of August, 1999

*Attest:*

Q. TODD DICKINSON

*Attesting Officer*  Acting Commissioner of Patents and Trademarks